(12) United States Patent
Kormanyos

(10) Patent No.: US 8,154,308 B2
(45) Date of Patent: Apr. 10, 2012

(54) METHOD FOR CHARACTERIZING INTEGRATED CIRCUITS FOR IDENTIFICATION OR SECURITY PURPOSES

(75) Inventor: Brian K. Kormanyos, Edmonds, WA (US)

(73) Assignee: The Boeing Company, Chicago, IL (US)

( * ) Notice: Subject to any disclaimer, the term of this patent is extended or adjusted under 35 U.S.C. 154(b) by 913 days.

(21) Appl. No.: 11/559,361

(22) Filed: Nov. 13, 2006

(65) Prior Publication Data

US 2008/0111561 A1     May 15, 2008

(51) Int. Cl.
*G01R 35/00* (2006.01)
*G01R 27/04* (2006.01)
*G01R 31/20* (2006.01)
*G01R 31/14* (2006.01)

(52) U.S. Cl. .................. 324/638; 324/601; 324/750.18; 702/117

(58) Field of Classification Search .................. 324/638, 324/750.15, 750.18
See application file for complete search history.

(56) References Cited

U.S. PATENT DOCUMENTS

| | | | | |
|---|---|---|---|---|
| 4,803,419 | A | * | 2/1989 | Roos .............................. 324/642 |
| 5,003,253 | A | * | 3/1991 | Majidi-Ahy et al. ......... 324/754 |
| 6,049,219 | A | * | 4/2000 | Hwang et al. ................. 324/765 |
| 6,100,703 | A | * | 8/2000 | Davidov et al. .............. 324/631 |
| 7,150,184 | B1 | * | 12/2006 | Scott et al. ........................ 73/73 |
| 7,184,910 | B2 | * | 2/2007 | Lee et al. ...................... 702/104 |
| 7,519,878 | B2 | * | 4/2009 | Rosen ........................... 714/723 |
| 7,532,014 | B2 | * | 5/2009 | Chladek et al. ............... 324/601 |
| 2004/0201383 | A1 | * | 10/2004 | Anderson ...................... 324/600 |
| 2005/0093554 | A1 | * | 5/2005 | Wang et al. ................... 324/638 |
| 2005/0194981 | A1 | * | 9/2005 | Cole .............................. 324/615 |
| 2005/0238218 | A1 | * | 10/2005 | Nakamura .................... 382/128 |
| 2006/0153739 | A1 | * | 7/2006 | Hilderbrand et al. ...... 422/82.11 |
| 2006/0155498 | A1 | * | 7/2006 | Dunsmore et al. ........... 702/107 |

* cited by examiner

*Primary Examiner* — Jeff Natalini
(74) *Attorney, Agent, or Firm* — Yee & Associates, P.C.

(57) ABSTRACT

A method of detecting small changes to a complex integrated circuit measuring RF/microwave scattering parameters between every pin over a wide frequency range. The data from a characterization of a known good integrated circuit is stored and compared to each subsequent integrated circuit of unknown background.

9 Claims, 5 Drawing Sheets

METHOD FOR CHARACTERIZING INTEGRATED CIRCUITS FOR IDENTIFICATION OR SECURITY PURPOSES

BACKGROUND

1. Field of the Invention

This invention relates generally to RF/microwave measurement techniques used in integrated circuit testing, and even more specifically to the use of microwave scattering parameters(S parameters) in such techniques.

2. Related Art

In the post 9/11 world, there is an increased need for and concern about enhanced security. The security of state of art electronics systems ranks high among these concerns. The United States Department of Defense (DOD) recognizes the importance of assuring the protection of vital components of electronics systems from tempering by hostile forces. The DOD has launched a number of programs, via the Defense Advanced Research Projects Agency (DARPA), to address the issue. DARPA's concern is that the ability exists to detect small changes that might deliberately be introduced into an integrated circuit for hostile purposes.

Modern integrated circuits (ICs) are very complex devices and different methods may be used to introduce hostile changes, which would not be detected immediately by ordinary electrical testing. For example, long delay electronic counters connected to disable circuitry could be introduced. Other changes to reduce electrical reliability by changing feature sizes may also be introduced.

Changes to an integrated circuit may occur at an untrusted stage of the design or manufacturing. The changes may include modifying the RTL (register transfer level), the netlist, the layout, the fabrication process, or even the silicon, for example, by using Focused Ion Beam (FIB) editing. An untrusted foundry may make logic insertions or modifications, or include IP cores, which contain parasitic features used to sabotage normal operations by changing delays, or disabling clocks or busses.

It might be desirable to identify particular integrated circuits, or parts of integrated circuits for the protection of intellectual property rights.

Therefore, a need exists for non-destructive methods to provide highly sensitive and selective detection of even very subtle modifications that appear anywhere in the IC lifecycle.

SUMMARY

The present invention provides a method for characterizing an integrated circuit. The method employs a microwave scattering parameter measurement technique that allows for the detection of tampering with ICs, which may occur during design and production cycles.

In one aspect of the present invention, a method is provided which includes stimulating a pin of an un-powered circuit direct RF probing, while measuring the RF energy that is reflected back on the input signal and measuring the RF energy that is present on the other pins. The measurement is repeated for every pin of the circuit. The generated measurement data represents a unique fingerprint of the circuit.

In another aspect of the present invention, a method is provided for using polarimetric millimeter-wave radar techniques The method includes a waveguide that is placed in contact with the back of the IC or close to the front and mechanically scanned in two dimensions. Reflected signals are measured in both polarizations, the signal coupled to the IC pins are also measured Alternatively, a bi-static methods with a separate transmit and receive waveguide probe may also be used to monitor reflections in directions other than directly back toward the transmitter. Millimeter wave signals passing through the chip may also be measured in both polarizations with a second waveguide probe.

Yet another aspect of the present invention includes a method for verifying the authenticity of an integrated circuit of unknown background. The method includes characterizing an integrated circuit of known pedigree, characterizing an integrated circuit of unknown background, and comparing the fingerprints of the two integrated circuits. The method of characterization can include either of the methods described above.

The present invention allows for the use of a variety of comparison techniques, for example, it can use a simple visual graphic comparison, or a sophisticated pattern recognition technique, depending on the complexity of the ICs being verified.

The comparison of fingerprints for large and complex ICs requires extensive data processing. Pattern recognition techniques, such as dynamic time wrapping and back projection, originally developed for RADAR, speech recognition, and medical imaging may be used to make these comparisons.

The present invention provides a low cost, non-destructive method of assuring complex electronic hardware security that does not exist today. Any company or agency that desires to provide security testing of electronic hardware or to detect intellectual property violations can do so by using this low cost method, rather than traditional reverse engineering.

This brief summary has been provided so that the nature of the invention may be understood quickly. A more complete understanding of the invention can be obtained by reference to the following detailed description of the embodiments thereof in connection with the attached drawings.

BRIEF DESCRIPTION OF THE DRAWINGS

The foregoing features and other features of the present invention are described with reference to the drawings. In the drawings, the same components have the same reference numerals. The illustrated embodiments are intended to illustrate, but not to limit the invention. The drawings include the following Figures.

DETAILED DESCRIPTION

The invention provides a method of using microwave signals to determine the characteristics of an integrated circuit (IC) such that the IC can be readily identified and any unexpected changes in the IC can be detected. In one embodiment, the invention provides a method for measuring microwave scattering parameters (S parameters) between pin pairs of a large integrated IC.

The S parameters represent the ratios between incident and reflected or transmitted waves. Because of the complex leakage paths and material interactions in an IC, if microwave signals are applied to the pins of the IC, a unique S parameter fingerprint may be identified and the data representing the fingerprint obtained. A collection of S parameter data obtained across a wide frequency range allows unique identification of the IC, thus detection of very small changes to the make up of the IC is possible.

Figure 1:
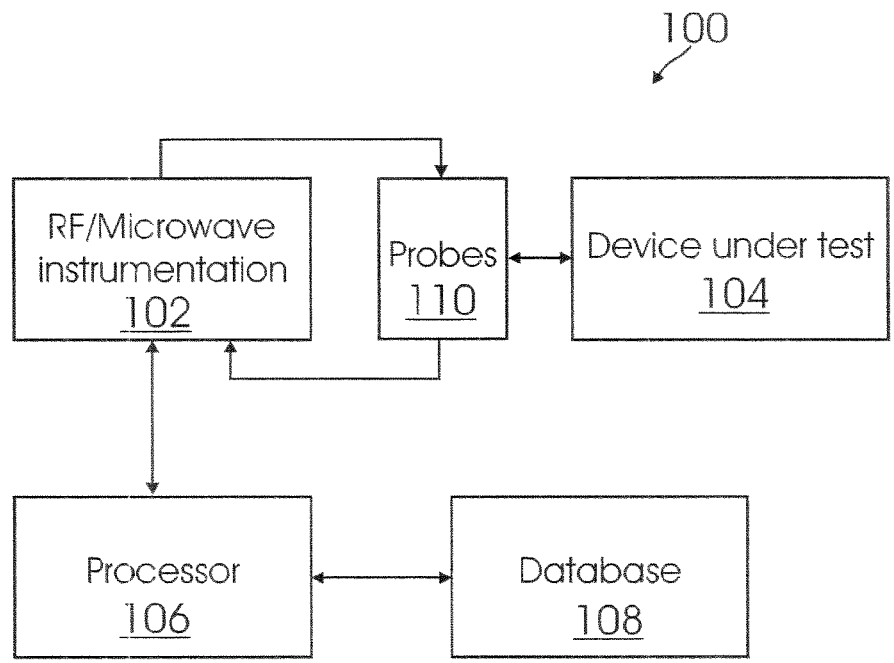
FIG. 1 is a block diagram illustrating a setup used for IC characterization.

Various RF/microwave scattering parameters, including amplitude and phase information for reflected and transmitted signals, are measured using equipment with a dynamic range exceeding 60 dB. RF/microwave scattering parameters in a complex digital circuit are the functions of direct and indirect signal paths between the pins FIG. 1 is a block diagram illustrating a setup used for IC characterization. Test setup 100 includes a network analyzer 102, such as RF/Microwave instrumentation, coupled to a device under test (DUT) 104, such as an IC, which is to be characterized via a probing means 110. Test setup 100 also includes a processor 106 used for controlling and interacting with network analyzer 102, and database 108 for storing characterization results data.

Figure 2:
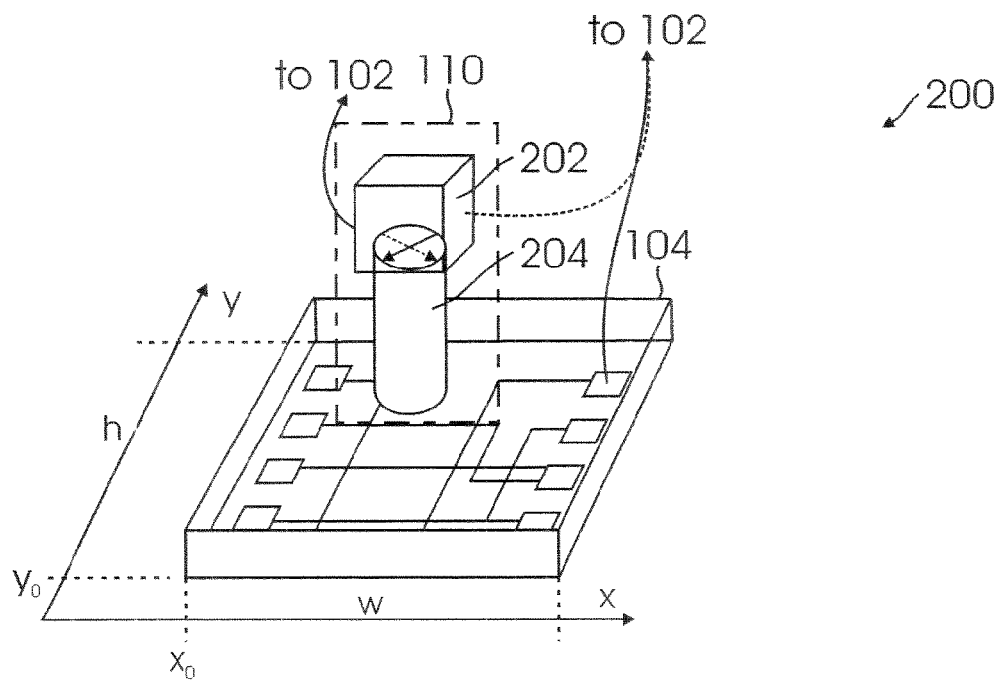
FIG. 2 is a simplified diagram illustrating a setup for IC characterization using a wave-guide probing technique in accordance with an embodiment of the present invention.

FIG. 2 is a simplified diagram illustrating a probing setup 200 for IC characterization using a wave-guide probing technique in accordance with an embodiment of the present invention. In this embodiment, probing setup 200 includes one or more circular waveguides 204 producing dual polarized electromagnetic radiation. Circular waveguide 204 is attached to a 2D X-Y translation stage 202 and coupled to network analyzer 102 via a coax adapter (not shown).

In one embodiment, circular waveguide 204 operates in the range of 25-100 GHz to support two orthogonal polarizations. Waveguide 204 is dielectrically loaded to match the feature size of DUT 104 to achieve an illumination face diameter about 1 mm. In operation, waveguide 204 is placed in contact with a backside of DUT 104 or alternatively placed close to the front side of DUT 104. The DUT 104 is mechanically scanned by moving of translation stage 202 carrying the waveguide 204 to move in the x and y direction during characterization.

Figure 3:
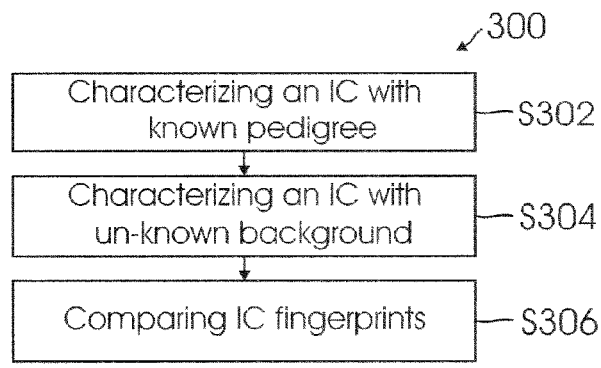
FIG. 3 is a flowchart illustrating a method of verifying the authenticity of an IC in accordance with an embodiment of the present invention.

FIG. 3 is a flowchart illustrating a method 300 for verifying the authenticity of a DUT in accordance with an embodiment of the present invention. Referring now to FIGS. 1 and 3, in step s302, DUT 104, such as an IC with a known pedigree is characterized, to create a "trusted" RF fingerprint. RF instrumentation 102 using probing means 110 is applied to DUT 104. The resulting RF fingerprint data is than stored as a "trusted fingerprint" in database 108.

In step s304, when a new DUT 104 is to be verified for authenticity, the new DUT 104 is probed using an identical characterization process to that used in step s302 to create the trusted fingerprint. The result is a new fingerprint representing new DUT 104.

In step s306, the trusted fingerprint is compared to the new fingerprint. A match of the fingerprint characteristics points to the authenticity of the new DUT 104.

Figure 4:
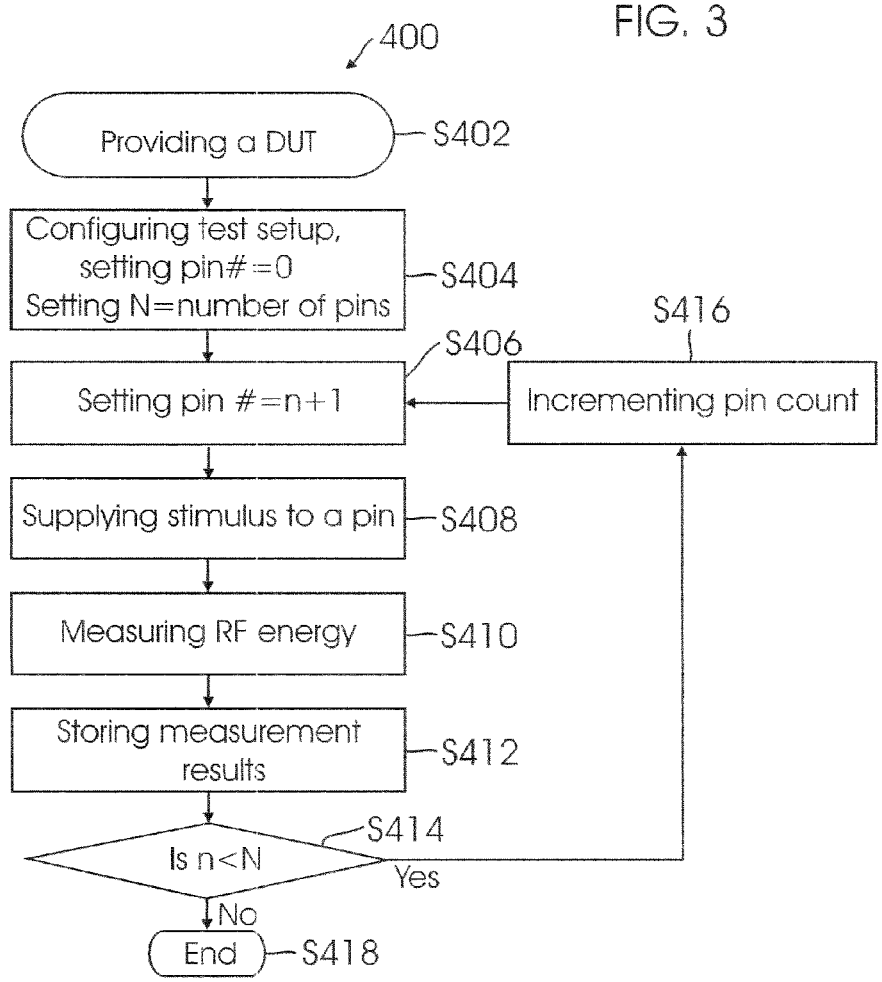
FIG. 4 is a flowchart illustrating a method of characterizing an IC.

FIG. 4 is a flowchart illustrating a method 400 of characterizing an IC. Method 400 is used for characterizing an IC using a probing technique, where probes are directly connected to DUT 104.

In steps s402-s406 a DUT 104 is provided for testing and testing parameters and conditions for DUT 104 are set and configured.

In step s408, a stimulus is supplied to DUT 104, for example, RF signals are coupled to pin pairs of a not "powered on" IC. When microwave radiation moves across the IC, via leakage paths, parasitic coupling and reflection from discontinuities between the metal, polysilicon, and transistor devices influence the microwave signal depending on their size and location. The response to this stimulus is captured in step s410, since the amplitude and phase of each signal path is a function of the frequency. Over a wide frequency range, many simultaneous paths result in a superposition of signals, whose amplitude and phase change significantly with the frequency, resulting in a unique signature for each IC or part of an IC. It should be understood that steps s408 and s410 may not be two distinct events in time, but rather occur simultaneously.

In step s412, measurement results are stored for future processing in steps s414 and s416, it is determined to repeat steps s408-s412 until all pin pairs of the IC have been tested.

By testing all IC pin pairs, method 400 collects, analyzes, and correlates a large raw microwave S parameter data set. This data set is the RF fingerprint. The RF fingerprint uniquely characterizes a particular circuit implementation.

Another set of fingerprint data my be obtained by transforming amplitude and phase scattering data over a frequency range, into time domain using Fourier transform, where gating and inverse transform methods may be used to remove the effects of certain discontinuities or to examine particular areas of DUT 104, based on the effective propagation time of the RF/microwave signals.

Figure 5:
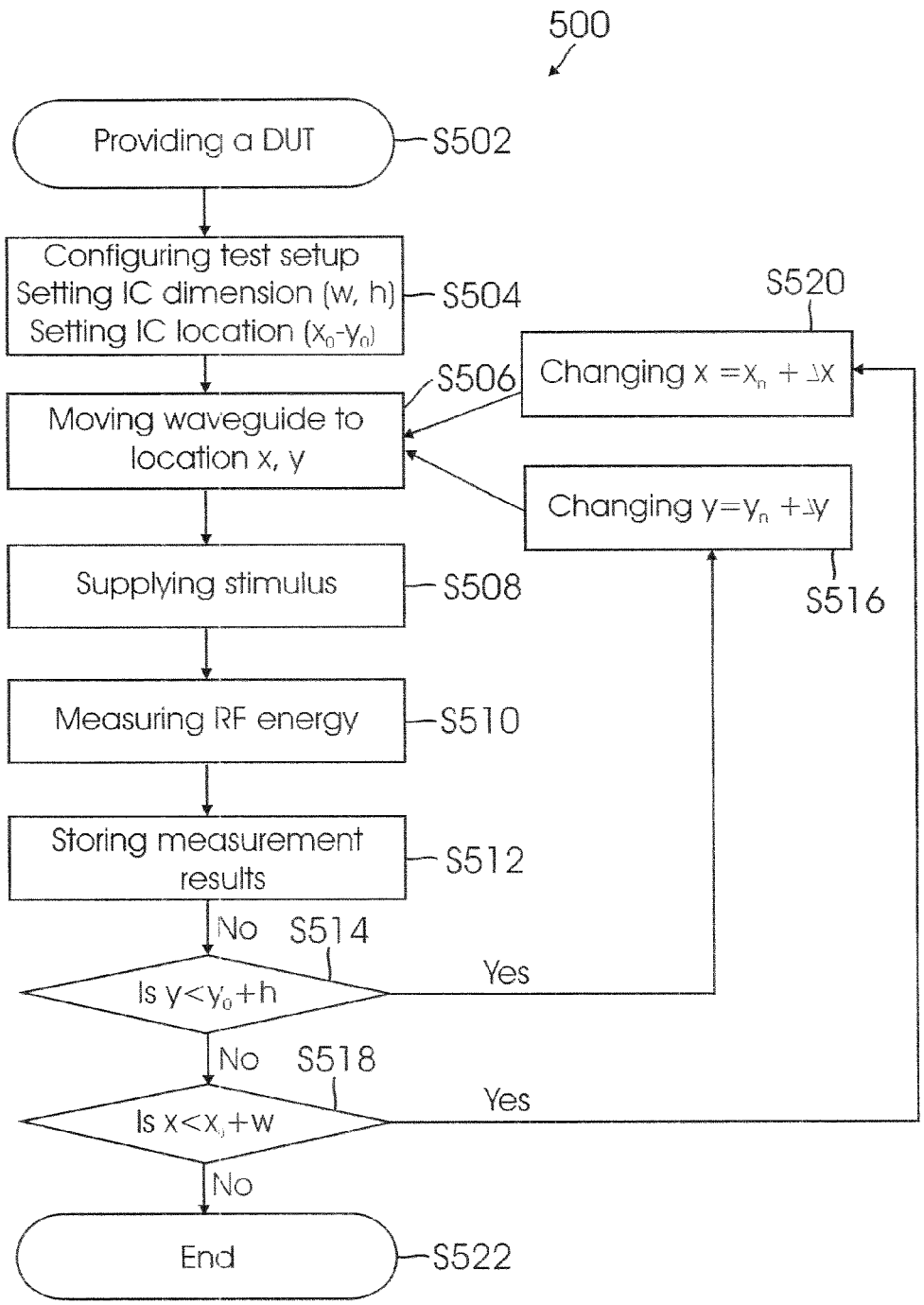
FIG. 5 is a flowchart illustrating a method of characterizing an IC using wave-guide probing technique in accordance with an embodiment of the present invention.
Figure 6:
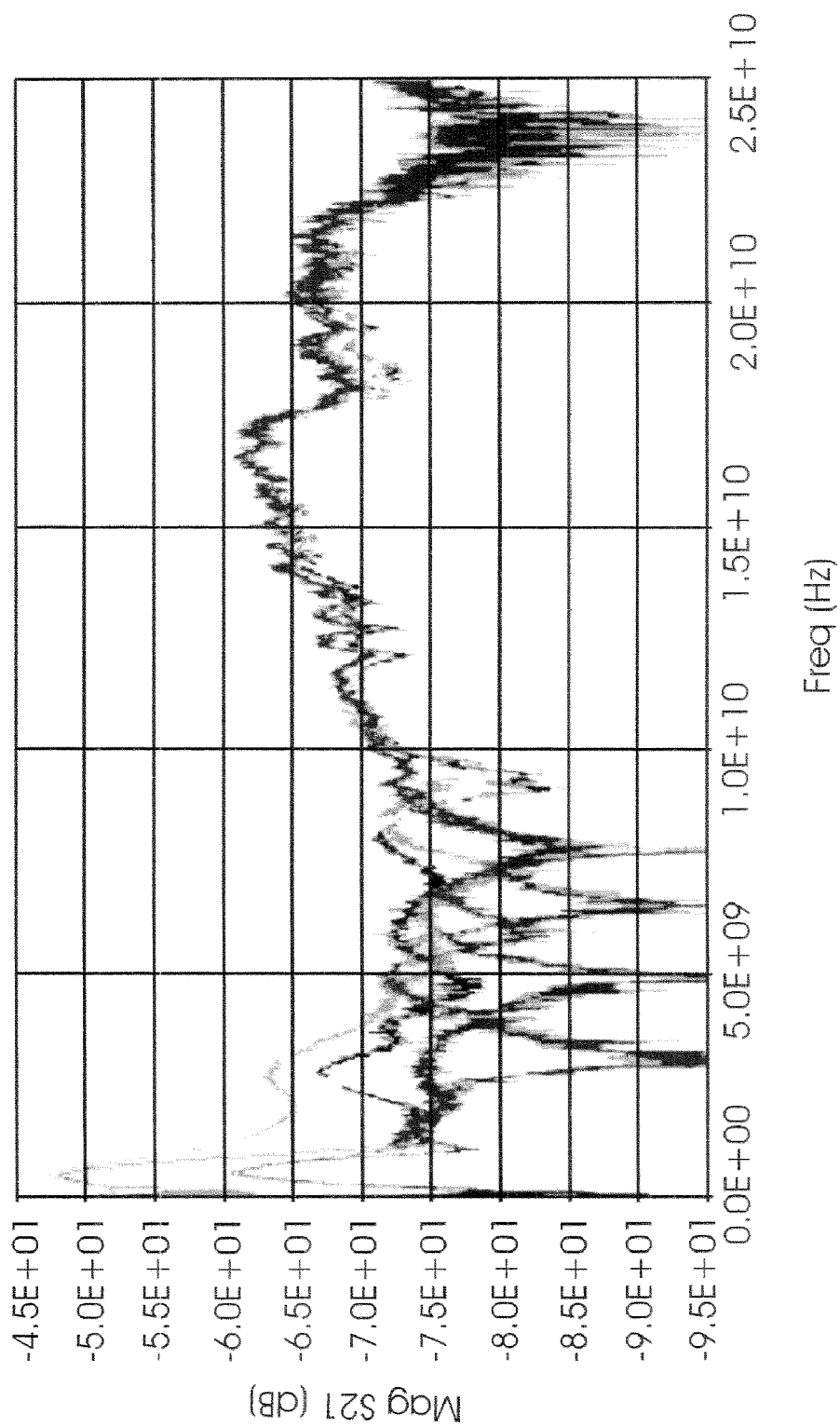
FIG. 6 is a graph representing a frequency domain "RF fingerprint" obtained measuring multiple pins in accordance with an embodiment of the present invention.
Figure 7:
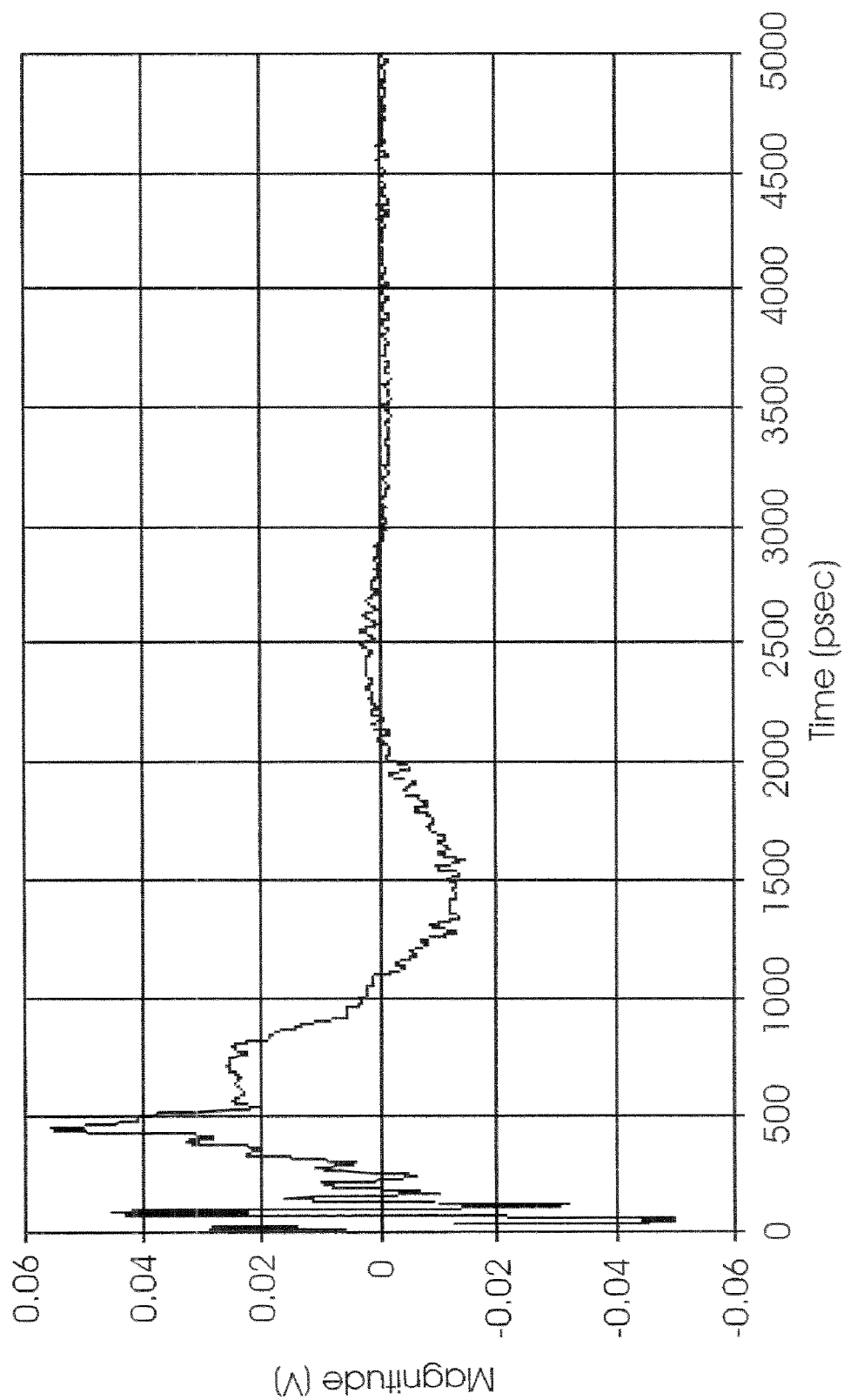
FIG. 7 is a graph representing a time domain "RF fingerprint" obtained measuring one pin in accordance with an embodiment of the present invention.

FIG. 5 is a flowchart illustrating a method of characterizing an IC using wave-guide probing technique in accordance with an embodiment of the present invention. Method 500 includes characterizing an IC using a waveguide based probing technique, for example, where dual polarized waveguide 204 (FIG. 2) is coupled to DUT 104.

Referring now to FIGS. 2 and 5, the characterization method in steps s502-s500 sets up the IC testing by providing a DUT and configuring test conditions, such as IC dimensions, and IC location.

In step s508, RF signals are coupled to the backside of DUT 104 via circular waveguide 204. Circular waveguide 204 couples a swiping stimulus in the range of 25-100 GHz with two orthogonal polarizations. Wavelengths may be selected such that the signals are not blocked by silicon or metal fill patterns.

In steps s510 and s512 signals for both polarization states at all frequencies, both reflected back toward the source and transmitted to every pin, are measured and recorded.

In step s514, it is determined to repeat steps s508-s516 until DUT 104 is scanned in its whole length (h) in a y direction.

In step s516, waveguide 204 is moved to a new location on DUT 104

In step s518, it is determined to repeat steps s506-s512 until DUT 104 scanned in its whole width (w) x direction.

In steps s520, waveguide s204 is again moved to a new location on DUT 104 and the scanning continues.

After DUT 104 is completely scanned, in step s522, the test ends.

In another embodiment of the present invention RF characterization can be performed on operating ICs. While the IC is being exercised by a predetermined logic stimulus, RF/microwave signals may be applied to some pins of the IC through bias tees. This dynamic characterization can further enhance detection sensitivity.

The RF/microwave power level applied during the characterization may be controlled, assuring that the test is non-destructive. Existing microwave network analyzer equipment is used to perform the characterization.

Although the present invention has been described with reference to specific embodiments, these embodiments are illustrative only and not limiting. Many other applications and embodiments of the present invention will be apparent in light of this disclosure and the following claims.

What is claimed is:

1. A method for characterizing an unpowered integrated circuit comprising:
   obtaining a first data set by coupling a first RF-input stimulus signal to each first pin pair of a known integrated circuit having a plurality of first pin pairs, and, for each coupling, measuring and recording a first RF energy reflected back from the known integrated circuit on the first RF-input stimulus signal and a plurality of first RF energy levels at all other first pin pairs of the plurality of first pin pairs;
   creating a fingerprint for the known integrated circuit by collecting, analyzing, and correlating the first data set;
   providing a test device having a backside and including a plurality of second pin pairs, wherein the test device is the unpowered integrated circuit;
   obtaining a second data set by coupling a second RF-input stimulus signal to each second pin pair of the plurality of second pin pairs and for each coupling measuring and recording a second RF energy reflected back from the test device on the second RF-input stimulus signal and measuring and recording a plurality of second RF energy levels at all other second pin pairs of the plurality of second pin pairs;
   creating a test device fingerprint for the test device by collecting, analyzing, and correlating the second data set; and
   comparing the fingerprint to the test device fingerprint to determine if the test device has been modified to differ from a configuration of the known integrated circuit.

2. The method of claim 1, further comprising:
   performing measurements to form the test device fingerprint by a network analyzer and a waveguide probe.

3. The method of claim 1, wherein coupling the RF-input stimulus signal to the test device comprises coupling the RF-input stimulus signal to the test device via a hard-wire connection to one of the plurality of pins.

4. The method of claim 1, wherein coupling the RF-input stimulus signal to the test device comprises coupling the RF-input stimulus signal to the test device via a waveguide placed in contact with the backside of the test device and mechanically scanned in two directions.

5. The method of claim 4, wherein the waveguide comprises a circular, dual polarized waveguide.

6. The method of claim 4, wherein the waveguide is dielectrically loaded.

7. The method of claim 1 wherein the comparing the fingerprint to the test device fingerprint to determine if the test device has been modified to differ from a configuration of the known integrated circuit is performed using one of a speech recognition technique and a medical imaging technique.

8. An apparatus for characterizing an unpowered integrated circuit comprising:
   a known integrated circuit having a plurality of first pin pairs;
   means for obtaining a first data set by coupling a first RF-input stimulus signal to each first pin pair of the plurality of first pin pairs and, for each coupling, measuring and recording a first RF energy reflected back from the known integrated circuit on the first RF-input stimulus signal and a plurality of first RF energy levels at all other first pin pairs of the plurality of first pin pairs;
   means for creating a fingerprint for the known integrated circuit by collecting, analyzing, and correlating the first data set;
   a test device having a backside and including a plurality of second pin pairs, wherein the test device is the unpowered integrated circuit;
   means for obtaining a second data set by coupling a second RF-input stimulus signal to each second pin pair of the plurality of second pin pairs and, for each coupling, measuring and recording a second RF energy reflected back from the test device on the second RF-input stimulus signal and a plurality of second RF energy levels at all other second pin pairs of the plurality of second pin pairs;
   means for creating a test device fingerprint for the test device by collecting, analyzing, and correlating the second data set; and
   means for comparing the fingerprint to the test device fingerprint to determine if the test device has been modified to differ from a configuration of the known integrated circuit.

9. The apparatus of claim 8 wherein the means for comparing the fingerprint to the test device fingerprint to determine if the test device has been modified to differ from a configuration of the known integrated circuit includes one of a speech recognition technique and a medical imaging technique.

* * * * *